United States Patent
Józefiak et al.

(10) Patent No.: US 11,849,710 B2
(45) Date of Patent: Dec. 26, 2023

(54) PRODUCTION SURFACE WITH SYSTEM OF UNDERFLOOR HEATING AND/OR COOLING OF INSECT FEED, USE OF UNDERFLOOR SYSTEM AND METHOD FOR BREEDING INSECTS USING THEREOF

(71) Applicant: HiProMine S.A., Robakowo (PL)

(72) Inventors: Damian Józefiak, Robakowo (PL); Piotr Lubik, Poznań (PL); Krzysztof Dudek, Sędziny (PL)

(73) Assignee: HIPROMINE S.A., Robakowo (PL)

( * ) Notice: Subject to any disclaimer, the term of this patent is extended or adjusted under 35 U.S.C. 154(b) by 0 days.

(21) Appl. No.: 17/790,686

(22) PCT Filed: Jun. 29, 2021

(86) PCT No.: PCT/PL2021/050048
§ 371 (c)(1),
(2) Date: Jul. 1, 2022

(87) PCT Pub. No.: WO2021/235957
PCT Pub. Date: Nov. 25, 2021

(65) Prior Publication Data
US 2023/0172173 A1    Jun. 8, 2023

(30) Foreign Application Priority Data
Aug. 24, 2020 (PL) .......................... 435064

(51) Int. Cl.
*A01K 67/033*    (2006.01)
(52) U.S. Cl.
CPC .................. *A01K 67/033* (2013.01)
(58) Field of Classification Search
CPC .................................................. A01K 67/033
See application file for complete search history.

(56) References Cited

U.S. PATENT DOCUMENTS

2017/0311612 A1* 11/2017 Leo .......................... A21D 2/34
2018/0168133 A1*  6/2018 Taylor .................... A01K 61/85
(Continued)

FOREIGN PATENT DOCUMENTS

| CN | 210900995 | 7/2020 |
| ES | 2386472 | 8/2012 |
| PL | 418244 | 2/2018 |

OTHER PUBLICATIONS

International Search Report and Written Opinion for PCT/PL2021/050048 dated Sep. 29, 2021.

*Primary Examiner* — Monica L Perry
*Assistant Examiner* — Aaron M Rodziwicz
(74) *Attorney, Agent, or Firm* — Elizabeth L. Neal; DeWitt LLP

(57) ABSTRACT

A production surface for rearing and/or breeding insects and/or larval forms of insects includes at least one breeding surface used for breeding insects and laying out feed for the insects. An underfloor feed heating and/or cooling system with a closed flow of heating-cooling medium is used for heating/cooling the feed on the breeding surface. A method for breeding insects uses such a production surface for rearing and/or breeding insects and/or larval forms of insects. Another method for breeding insects lays out feed on the breeding surface and uses an underfloor feed heating and/or cooling system to heat and/or cool the feed. Such a method uses a heated production surface for rearing and/or breeding insects and/or larval forms of insects. The heated production surface features an electrical underfloor feed heating system.

36 Claims, 7 Drawing Sheets

(56) References Cited

U.S. PATENT DOCUMENTS

2022/0304287 A1\* 9/2022 Van Kilsdonk ...... A01K 67/033
2022/0306404 A1\* 9/2022 De Wolf .............. A01K 67/033

\* cited by examiner

A

B

PRODUCTION SURFACE WITH SYSTEM OF UNDERFLOOR HEATING AND/OR COOLING OF INSECT FEED, USE OF UNDERFLOOR SYSTEM AND METHOD FOR BREEDING INSECTS USING THEREOF

TECHNICAL FIELD

The object of the invention is a production surface with at least one breeding surface with an underfloor feed heating and/or cooling system placed therein for use in different types of breedings, for breeding in containers and on breeding surfaces, on a production line for rearing and/or breeding insects and/or larval forms comprising such a production surface. The invention also relates to a method for breeding insects including a step of rearing and/or breeding insects and/or larval forms of insects using a production surface with an underfloor feed heating and/or cooling system. The said system uses an underfloor type heating/cooling in a closed system and a medium in the form of water, glycol or others. Another object of the invention is a method for breeding insects including the steps of: laying the feed, heating/cooling the laid insect feed, and using an underfloor feed heating and/or cooling system to heat and/or cool the feed on the breeding surface. Another object of the invention is a heated production surface for rearing and/or breeding insects and/or larval forms of insects, which uses an electrical underfloor heating system, use thereof and a method for breeding using thereof.

The invention using a feed heating and/or cooling system is particularly adapted for rearing and/or breeding insects and/or larval forms of insects of the order Coleoptera and/or Diptera.

STATE OF ART

In recent years, industrial insect breeding has been indicated as an environmentally sustainable alternative for the production of protein and fat for feed purposes including feeding of livestock and for food purposes (Food and Agriculture Organization of the United Nations 2012 Assessing the potential of insects as food and feed in assuring food security. Summary report. Technical consultation meeting 23-25 January, FAO, Rome, Italy).

A group of insects with a particular potential as a source of protein for feed and food purposes are beetle larvae (Coleoptera) from the darkling beetle family (Tenebrionidae) and hymenopteran larvae (Diptera). Among the species bred on a semi-industrial and industrial scale, species to be mentioned are: lesser mealworm (*Alphitobius diasperinus*), mealworm (*Tenebrio molitor*), superworm (*Zophobas morio*), confused flour beetle (*Tribolium confusum*), red flour beetle (*Tribolium castaneum*), black flour beetle (*Tribolium madens*), and other species of the darkling beetle family and Hymenoptera from species belonging to the genus *Hermetia* (*Hermetia illucens*). All the above mentioned species feed in the substrate at the larval growth stage.

Currently used technologies for breeding of darkling beetle larvae are based on "rack systems", or self-supporting ones using containers with a small surface area with a few centimeters (1-5 cm) thick layer of breeding substrate (described e.g. in the international application PCT WO2014171829A1).

As a standard, plastic containers or transport boxes placed on pallets are used for breeding (described e.g. in the application PCT/FR2016/050849). These usually have a small container area, generally not exceeding 0.5 m². Therefore, the solutions used make it difficult to precisely control the microclimate due to poor gas exchange and removal of moisture and excess metabolic heat, etc. Thermal conditions can change dramatically over short periods of time, e.g. due to the temperature of the provided feed or the handling of containers with insects, as well as due to the metabolism of the insects themselves, i.e. so-called specific dynamic heat losses or excesses due to metabolic heat. From the point of view of animal welfare, and especially of insects, which are exothermic animals, unstable environmental conditions are associated with stress and may cause changes in feed intake or growth rates. Drawer and container rearing systems entail the need for heating of the entire room in which the insects are housed. Often breeding is also carried out directly on the insulated floor of the breeding room. As the species bred belong to thermophilic organisms, the solutions used so far make it necessary to maintain a high air temperature reaching over 30° C. throughout the entire rearing period, though for proper development of the insects it is not advisable to keep them at temperatures above 35° C., especially above 42° C., as this leads to overheating of the insects, which in the case of large-cubature breeding rooms generates high energy consumption, most of which is lost in heating and/or cooling of the air and the room elements themselves and not the insects themselves. Furthermore, heating and/or cooling of the breeding itself, i.e. the insects and/or the feed, requires heating and/or cooling of the entire breeding room. This, in addition to the energy expenditure, necessitates the use of equipment with high heating and/or cooling capacity, which translates significantly into the cost of breeding insects per one square meter or cubic meter of heated/cooled cubature. Such a method of heating and/or cooling also does not ensure an accurate temperature of the heated and/or cooled breeding/feed over a large breeding surface. Apart from the energy intensity of the breeding process, drying of the biomass after fattening is an equally important problem with the currently known methods. For the larvae to be able to be sieved well from the fertilizer, the moisture content of the whole sieved mass must be lower.

From the Polish patent description PL230275B1, solutions are known in the form of a modular, multi-storey system of technological lines with multi-storey breeding surfaces. However, said lines do not provide heating or cooling of feed.

DISCLOSURE OF INVENTION

The aim of the invention is to overcome the abovementioned disadvantages resulting from the state of the art. This aim has been achieved by unexpectedly observing that the provision of insect feed in the form of heated and/or cooled feed by an engineered system of underfloor heating and/or cooling of the breeding surface based on underfloor heating and/or cooling in a closed system being part of an engineered production line or breeding line, allows indirect heating and/or cooling of the insect organisms and their environment regardless of the cubature of the breeding room, thus increasing the fattening rate of the insects, whilst reducing feed consumption per kg of animal body weight gain (FCR), and ensuring stabilization of other parameters such as ambient temperature and humidity, thus stabilizing housing parameters, ensuring optimum environmental conditions, including breeding temperature, and optimizing the results and conditions of insect breeding.

The inventors of the present solution have found that it is preferable to use an underfloor heating and/or cooling system installed in breeding surfaces to heat and/or cool the provided feed, which then serves as a source of heat or a cooling agent for the insects or insect larvae feeding therein. The system allows precise control of thermal conditions in insect breeding, while minimizing energy losses through heating and/or cooling of unnecessary spaces.

A production surface for rearing and/or breeding of insects and/or larval forms of insects or a breeding line by integration with an underfloor feed heating and/or cooling system increases the rearing efficiency by providing stable thermal conditions for the insects and insect larvae. In a preferred embodiment of the underfloor system, when used to heat feed placed directly in the production surface, the system allows a relatively low temperature to be maintained inside the breeding rooms, as the insects assimilate the heat necessary for their development by taking up the heated food.

In the case where an underfloor feed heating and/or cooling system is used to cool the feed placed directly in the production surface, the system allows to maintain a relatively stable optimum breeding temperature, as the insects are cooled by the intake of suitably cooled food whilst cooling of the whole cubature of the breeding room is not required.

A production surface with an underfloor heating and/or cooling system ensures stabilization and optimization of thermal conditions for breeding insects and allows a temperature-optimized breeding, in particular a zone-based optimization, depending on whether it is the growth phase or the species of insect, or whether it is the production zone or phase. Thus, a production surface with an underfloor heating and/or cooling system for the feed laid on the surface indirectly causes heating and/or cooling of the animals themselves. Currently, there are no alternative solutions to ensure the optimization of temperature conditions for insect breeding by transferring heat or receiving it from the insects themselves, larvae in insect production that would not relay on heating and/or cooling the breeding rooms and not be associated with significant energy losses and considerable energy expenditure, making such breeding economically and ecologically unviable.

The first object of the invention is a production surface for rearing and/or breeding insects and/or larval forms of insects, characterized in that it comprises:
a) at least one breeding surface for breeding insects for laying feed thereon, wherein preferably the breeding surface comprises at least one storey, which constitutes an autonomous conveyor belt, preferably with profiled lateral sidewalls arranged bilaterally along the direction of movement of the conveyor belt, preferably the edges of the lateral sidewalls are bent inwards,
b) an underfloor feed heating and/or cooling system with a closed flow of heating-cooling medium for feed heating and/or cooling on a breeding surface, wherein the underfloor feed heating and/or cooling system with a closed flow comprises at least one heating-cooling medium supply circuit and at least one heating-cooling medium return circuit connected to each other, and the heating-cooling medium supply circuit and the heating-cooling medium return circuit are fluidly connected to a heat exchanger for heating and/or cooling the heating-cooling medium, and the heating-cooling medium supply circuit and the heating-cooling medium return circuit comprise heating-cooling medium distributors, and heating-cooling pipes made of thermally conductive material for the distribution of heat and/or cold on the breeding surface are connected to the heating-cooling medium distributor via a shut-off valve, wherein the heating-cooling pipes made of thermally conductive material of the system for feed heating and/or cooling on the breeding surface are permanently integrated into at least one breeding surface for laying the feed for breeding insects thereon, wherein the heating-cooling pipes made of thermally conductive material are arranged in at least two rows parallel to each other, wherein the heating-cooling medium supply circuit and the heating-cooling medium return circuit are connected via a three-way valve, wherein rearing and/or breeding of insects and/or larval forms of insects concerns insects of the orders Coleoptera and/or Diptera.

In a preferred embodiment of the production surface, the cooling-heating medium is water or glycol.

In a further preferred embodiment of the production surface, the heat exchanger provides heating and/or cooling of the heating-cooling medium to a temperature in the range of 7-50° C., preferably 15-50° C.

In an another preferred embodiment of the production surface, the breeding surface is made of a material with good thermally conductive properties including copper, steel, aluminum, synthetic material, ceramic, concrete, preferably stainless steel.

In an another preferred embodiment of the production surface, the heating-cooling pipes are made of a material with good thermally conductive properties including copper, steel, aluminum, synthetic material, preferably synthetic material.

In yet further preferred embodiment of the production surface, the heat exchanger is based on a source of electrical energy, gas or the use of heat pumps or recuperation.

In a further preferred embodiment of the production surface, the heating-cooling pipes arranged on the breeding line form at least two rows of heating-cooling pipes spaced from each other, preferably spaced by from 1 to 20 cm.

In yet another preferred embodiment of the production surface, the heating-cooling medium supply circuit and the heating-cooling medium return circuit comprise a system of shut-off valves, drain valves, vents, at least one temperature sensor and at least one pressure sensor, and they are fluidly connected to each other.

In yet further preferred embodiment of the production surface, the heating-cooling medium return circuit includes a rotameter.

In a further preferred embodiment of the production surface, the heating-cooling medium supply circuit includes a solid particle filter.

In yet further preferred embodiment of the production surface, the fluid connection is provided by pipes made of steel.

The second object of the invention is a method for breeding insects including a step of rearing and/or breeding insects and/or larval forms of insects, said step in which the feed is heated and/or cooled by means of underfloor feed heating and/or cooling with a closed flow of heating-cooling medium for heating the feed on the breeding surface, wherein the step of rearing and/or breeding insects and/or larval forms of insects is carried out on the production surface defined in the first object of the invention.

A further object of the invention is a method for breeding insects including the steps:
the feed at storage temperature is laid onto a breeding surface adapted for laying feed for breeding insects thereon, wherein preferably the breeding surface comprises at least one storey, provided with an autonomous conveyor belt, preferably with profiled lateral sidewalls arranged bilaterally along the direction of movement of the conveyor belt, preferably the edges of the lateral sidewalls are bent inwards,
the feed for insects laid on the breeding surface adapted for laying feed for insects thereon is heated and/or cooled by an underfloor heating and/or cooling system in a closed system for heating and/or cooling the feed on the breeding surface, wherein the heating and/or cooling system includes:
at least one heating-cooling medium supply circuit and at least one heating-cooling medium return circuit connected to each other, and the heating-cooling medium supply circuit and the heating-cooling medium return circuit are fluidly connected to a heat exchanger for heating and/or cooling the heating-cooling medium, and the heating-cooling medium supply circuit and the heating-cooling medium return circuit comprise the heating-cooling medium distributors, and to the heating-cooling medium distributor via a shut-off valve the heating-cooling pipes made of thermally conductive material are connected for distribution of heat/cooling on the breeding surface constructed of thermally conductive material, wherein the heating-cooling pipes made of thermally conductive material of the system for the heating and/or cooling of the feed on the breeding surface are permanently integrated into at least one breeding surface for laying the feed for insect breeding thereon, wherein the pipes made of thermally conductive material are arranged in at least two rows parallel to each other, wherein the heating-cooling medium supply circuit and the heating-cooling medium return circuit are connected via a three-way valve, wherein rearing and/or breeding of insects and/or larval forms of insects concerns insects of the orders Coleoptera and/or Diptera.

In a preferred embodiment of the method for breeding insects the feed is heated to a temperature in the range of 15-50° C., more preferably 20-48° C., more preferably 25-35° C., more preferably 28-32° C.

In a further preferred embodiment of the method for breeding insects, the bred insects are placed in box, drawer or self-supporting systems.

In yet further preferred embodiment of the method for breeding insects, the heating medium is water or glycol.

In a preferred embodiment of the method for breeding insects, the heat exchanger ensures heating of the heating-cooling medium to a temperature in the range of 7-50° C., more preferably 15-50° C.

In an another preferred embodiment of the breeding method, the heating-cooling pipes are made of a material with good thermally conductive properties including copper, steel, aluminum, plastic, preferably plastic.

In an another preferred embodiment of the breeding method, the breeding surface is made of a material with good thermally conductive properties including copper, steel, aluminum, plastic, ceramic, concrete, preferably stainless steel. A breeding surface can be understood as a part of the floor or the whole floor of a room in which insect breeding is carried out. The breeding surface may, in this regard, be divided into smaller fragments by means of separators, where these can be partitions of various types of plastic or masonry. The breeding surface may also be lined with boxes, preferably with a bottom conducting heat well, for breeding insects. The breeding surface may be a multi-storey surface, e.g. as the described breeding surface of the modular, multi-storey technological line system known from PL230275B1. Such a surface may be provided with an autonomous conveyor belt, preferably with profiled lateral sidewalls bent inwards arranged bilaterally along the direction of movement of the conveyor belt and providing bio-assurance.

In yet another preferred embodiment of the breeding method, the heat exchanger is based on a source of electrical energy, gas or the use of heat pumps or recuperation. In a further preferred embodiment of the breeding method, the heating-cooling pipes arranged and integrated into the breeding surface form at least two rows of heating-cooling pipes spaced from each other, preferably by from 1 to 30 cm.

In yet further preferred embodiment of the breeding method, the heating-cooling medium supply circuit and the heating-cooling medium return circuit include a system of shut-off valves, drain valves, vents, at least one temperature sensor and at least one pressure sensor, and they are fluidly connected to each other.

In a preferred embodiment of the breeding method, the heating-cooling medium return circuit includes a rotameter.

In yet further preferred embodiment of the breeding method, the heating-cooling medium supply circuit includes a solid particle filter.

In a further preferred embodiment of the breeding method, the fluid connection is provided by pipes made of steel.

In a further preferred embodiment of the breeding method, the breeding surface is made of a material with good thermally conductive properties including copper, steel, aluminum, plastic, ceramic, concrete, preferably plastic.

The invention also relates to the use of an underfloor heating and/or cooling system with a closed flow for heating and/or cooling the feed on a breeding surface for breeding insects, wherein said system includes at least one heating-cooling medium supply circuit and at least one heating-cooling medium return circuit connected to each other, and the heating-cooling medium supply circuit and the heating-cooling medium return circuit are fluidly connected to a heat exchanger for heating and/or cooling the heating-cooling medium, and the heating-cooling medium supply circuit and the heating-cooling medium return circuit comprise the heating-cooling medium distributors, and to the heating-cooling medium distributor via a shut-off valve the heating-cooling pipes made of thermally conductive material are connected for distribution of heat on the breeding surface, wherein the pipes made of thermally conductive material of the system for the heating and/or cooling of the feed on the breeding surface are placed directly in the breeding surface, wherein the pipes made of thermally conductive material are arranged in at least two rows parallel to each other, wherein the heating-cooling medium supply circuit and the heating-cooling medium return circuit are connected via a three-way valve, wherein rearing and/or breeding of insects and/or larval forms of insects concerns insects of the orders Coleoptera and/or Diptera.

In a preferred embodiment of the use of the underfloor feed heating and/or cooling system, water or glycol is used as the heating-cooling medium.

In a further preferred embodiment of the use of the underfloor feed heating and/or cooling system, the heat exchanger provides heating of the heating-cooling medium to a temperature in the range of 15-50° C., more preferably 20-48° C., more preferably to 25-35° C., more preferably to 28-32° C. In a further preferred embodiment of the use of the underfloor feed heating and/or cooling system, pipes made of a material with good thermally conductive properties including copper, steel, aluminum, plastic, preferably plastic are used.

In yet another preferred embodiment of the use of the underfloor feed heating and/or cooling system, a heat exchanger based on an electrical or gas energy source or the use of heat pumps or recuperation is used.

In a preferred embodiment of the use of the underfloor feed heating and/or cooling system, the pipes are arranged in the breeding surface and permanently integrated therein (for example, poured with screed in the floor) forming at least two rows of pipes spaced from each other, preferably from 1 to 20 cm.

In an another preferred embodiment of the use of the underfloor feed heating and/or cooling system, the heating-cooling medium supply circuit and the heating-cooling medium return circuit are used, including a system of shut-off valves, drain valves, vents, at least one temperature sensor and at least one pressure sensor, and they are fluidly connected to each other.

In yet another preferred embodiment of the use of the underfloor feed heating and/or cooling system, the heating-cooling medium return circuit including a rotameter is used.

In yet further preferred embodiment of the use of the underfloor feed heating and/or cooling system, the heating-cooling medium supply circuit including a solid particle filter is used.

In a further preferred embodiment of the use of the underfloor feed heating and/or cooling system, pipes made of steel are used to create the fluid connection.

The invention also relates to a heated production surface for rearing and/or breeding insects and/or larval forms of insects, which comprises: at least one breeding surface for breeding insects for laying feed thereon, an underfloor feed heating system which constitutes an electrical underfloor heating system permanently placed in the breeding surface, wherein in a preferred embodiment the electrical underfloor heating system comprises a heating cable placed in the breeding surface connected via connection wires to a control-power unit controlling the operation of the heating cable, said control-power unit being connected to an energy source.

Preferred heated production surface for rearing and/or breeding of insects and/or larval forms of insects has an electrical underfloor heating system selected from a heating mat or heating cable.

The invention also relates to a method for breeding insects which includes a step of rearing and/or breeding insects and/or larval forms of insects, in which the feed is heated using a heated production surface for rearing and/or breeding insects and/or larval forms of insects, which comprises: at least one breeding surface for breeding insects for laying feed thereon, an underfloor feed heating system which is an electrical underfloor heating system permanently placed in the breeding surface, wherein in a preferred embodiment the electrical underfloor heating system comprises a heating cable placed in the breeding surface connected via connection wires to a control-power unit controlling the operation of the heating cable, said control-power unit being connected to an energy source.

In a preferred method for breeding insects, the electrical underfloor heating system is selected from a heating mat or heating cable.

The invention also relates to the use of a heated production surface according to the invention for heating the feed during rearing and/or breeding of insects and/or larval forms of insects from the orders Coleoptera and/or Diptera.

In a further preferred embodiment of the invention, the breeding surface is made of a material with good thermally conductive properties including copper, steel, aluminum, plastic, ceramic, concrete, preferably stainless steel.

Compared to known methods of providing insect larvae with an appropriate level of heat/cooling, the present invention is characterized by a much higher energy efficiency. The greatest advantage is the fact that it is no longer necessary to maintain a high temperature in the breeding rooms to heat the feed or to cool the entire cubature to lower the temperature of the insects and provide them with optimal thermal conditions. The ambient temperature can be in the range of 8° C. to 43° C. Due to the fact that the feed laid on the breeding surfaces is heated or cooled, the heating-cooling device used can be of much smaller capacity and consume less energy than in the case of heating/cooling of the entire room.

Another advantage is the speed and efficiency of heating/cooling. The feed in the system is heated in up to 12 hours from a temperature of 8° C. (the temperature of feed stored during cold periods of the year) to a temperature between 20° C. and 48° C., with the possibility of continuously adjusting it to regulate insect metabolism.

A great advantage of the underfloor feed heating and/or cooling system is also the possibility to adapt the system as well as the breeding surface according to the invention to a specific breeding surface, and so it can occupy up to 100% of the total breeding surface. There is no limitation to the size of the production surface, the underfloor feed heating and/or cooling system can even cover surfaces of more than 10,000 m$^2$ typical for the largest production halls as well as breedings carried out in small boxes or trays of less than 0.5 m$^2$.

The underfloor feed heating and/or cooling system in a closed system for heating the feed, which is particularly useful for indirect heating/cooling the feed and thus the bred insect larvae, includes the following elements A system of pipes of copper, steel, aluminum, synthetic material or other thermally conductive material including synthetic material, distributing the heating-cooling medium and providing heating/cooling of feed.

A heat exchanger providing heating/cooling of the medium in the pipes thanks to the use of energy from electrical and gas sources or based on heat pumps or recuperation and other sources of heat/cooling allowing to reach a temperature in the range of 7-50° C., more preferably 15-50° C. allowing to control metabolic processes of insects including specific dynamic heat losses or to ensure the removal of excess metabolic heat.

It has proven beneficial to use an underfloor feed heating and/or cooling system installed in breeding surfaces in order to heat/cool the provided feed, which then constitutes a source of heat/cooling for the insect larvae feeding therein. Underfloor feed heating and/or cooling systems and production surfaces comprising them allow precise control of thermal conditions in insect breeding, while minimizing energy wasted by heating/cooling unnecessary spaces. The possibility of heating/cooling the feed using an underfloor feed heating and/or cooling system can also be used to regulate feed moisture due to the increased evaporation of water from the feed of higher temperature when it is heated. This possibility has important practical consequences, because towards the end of insect fattening it is important to reduce feed moisture as much as possible, so that the process of sieving insects from the substrate can take place more efficiently. The feed laid on the line during insect fattening has a moisture content of up to 80%, while by heating the feed using an underfloor feed heating and/or cooling system or a heated production surface according to the invention for heating the feed, it is possible to dry it and reduce the moisture content at the end of fattening to a level of 20%. The feed laid on the breeding surfaces is in a layer thickness from 2 to 20 cm depending on the type of feed and species of insect.

Compared to previously used methods of providing insect larvae with an adequate level of heat, the solution according to the invention using an underfloor feed heating and/or cooling system installed in breeding surfaces for heating/cooling the fed feed is characterized by a much higher efficiency. The greatest advantage is that it is not necessary to maintain a high temperature in the breeding rooms for heating the feed or using cooling of large cubature for cooling the feed, and thus ensuring a suitable rearing temperature for the insects. The ambient temperature can be in the range of 8° C. to 43° C. As only the feed laid on the breeding surfaces is heated/cooled, the heating-cooling device used can be of a much lower capacity and energy consumption than that used to heat the entire room. In itself, the heating/cooling of feed using an underfloor feed heating and/or cooling system installed in the breeding surfaces is fast and effective. Feed in the system is heated within up to 12 hours from a temperature of 8° C. to a temperature between 20° C. and 48° C., with the possibility of continuously adjusting the temperature to regulate insect metabolism. Research carried out during testing of the prototype system has shown that feed in the described system heats up 6 to 12 times faster than in the open air, which translates into efficiency and speed of use of such a heating system in providing appropriate thermal conditions for insects. Moreover, the underfloor feed heating and/or cooling system, when used to heat or use the heated production surface to heat the feed, ensures that the temperature can be increased only on the surfaces which we want to dry, it is impossible with standard heating. As a result, insect biomass (preferably larvae) can be more easily sieved at further production stages.

Experiments carried out (Example 4) on *Hermetia illucens* have shown that insects bred using the technology described herein are characterized by a 7% faster fattening, understood as achieving a 7% higher body weight at the end of the fattening, as well as a 14% reduction in feed conversion ratio (FCR).

The abovementioned growth parameters as well as the FCR are closely correlated with the vital needs of the insects which have been shown to be 20-300% lower when using direct heating of feed on the breeding surfaces by an underfloor heating system. Moreover, the use of heated/cooled feed reduces the stress associated with feeding the larvae and increases their survival, which has been observed to be up to 45% higher when using a flow-through heating system compared to the standard rearing method where entire holding rooms are heated/cooled (Example 6). Thanks to the smooth regulation of the temperature of the fed feed, it is also possible to regulate the level of insects metabolism and, if necessary, shorten or lengthen its life cycle, as well as the FCR for both Coleoptera and Diptera insects. The possibility to heat the feed can also be used to regulate its moisture content thanks to the increased evaporation of water from the feed of higher temperature. For the above reasons, another function of the system is the drying of secondary metabolites after insect production including faeces, which are a component of the fertilizer.

An important advantage of production or breeding surfaces with an underfloor feed heating and/or cooling system is the fact that such a feed heating system can be used both in multi-level breeding surfaces such as multi-storey production lines which increases the available production space as well as when using a single level rearing system or even a "rack system". A great advantage is also the possibility of adapting the underfloor feed heating/cooling system to the breeding surface, so it can occupy up to 100% of the total production surface for rearing. There is no limitation to the size of the production surface (production or breeding lines with underfloor feed heating/cooling system), such a heating/cooling system can even occupy surfaces of more than 10,000 m$^2$ typical for the largest production halls as well as breedings carried out in small boxes or trays of less than 0.5 m$^2$.

DESCRIPTION OF THE FIGURES

The present invention has been illustrated in figures, which serve only to illustrate examples of the embodiment of the invention and do not limit its scope in any way.

EMBODIMENTS OF THE INVENTION

The following examples are included only to illustrate the invention and to explain its particular aspects, not to limit it, and should not be equated with the entire scope of the invention as defined in the appended claims.

EXAMPLES

Figure 1:
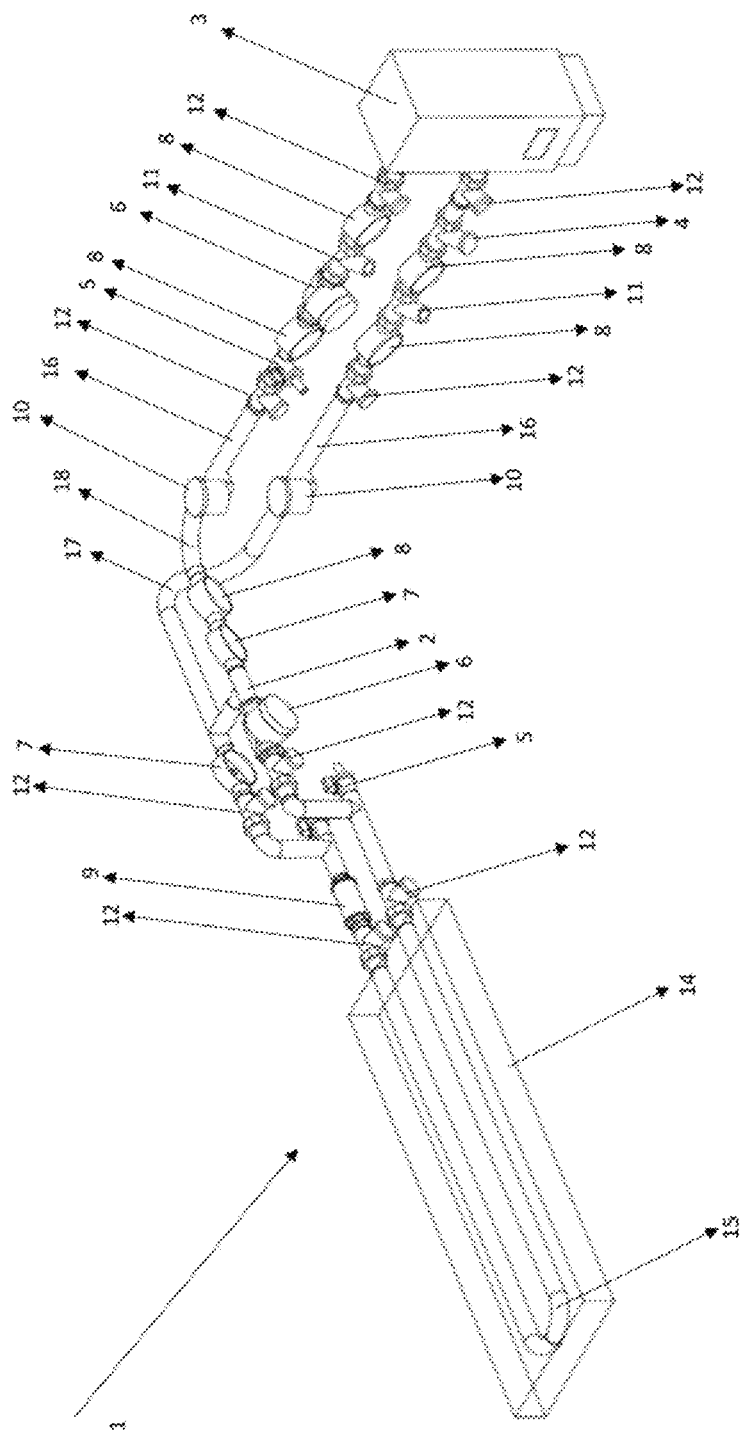
FIG. 1. shows a diagram of an underfloor heating and/or cooling system of a breeding surface for breeding invertebrates.
Figure 2:
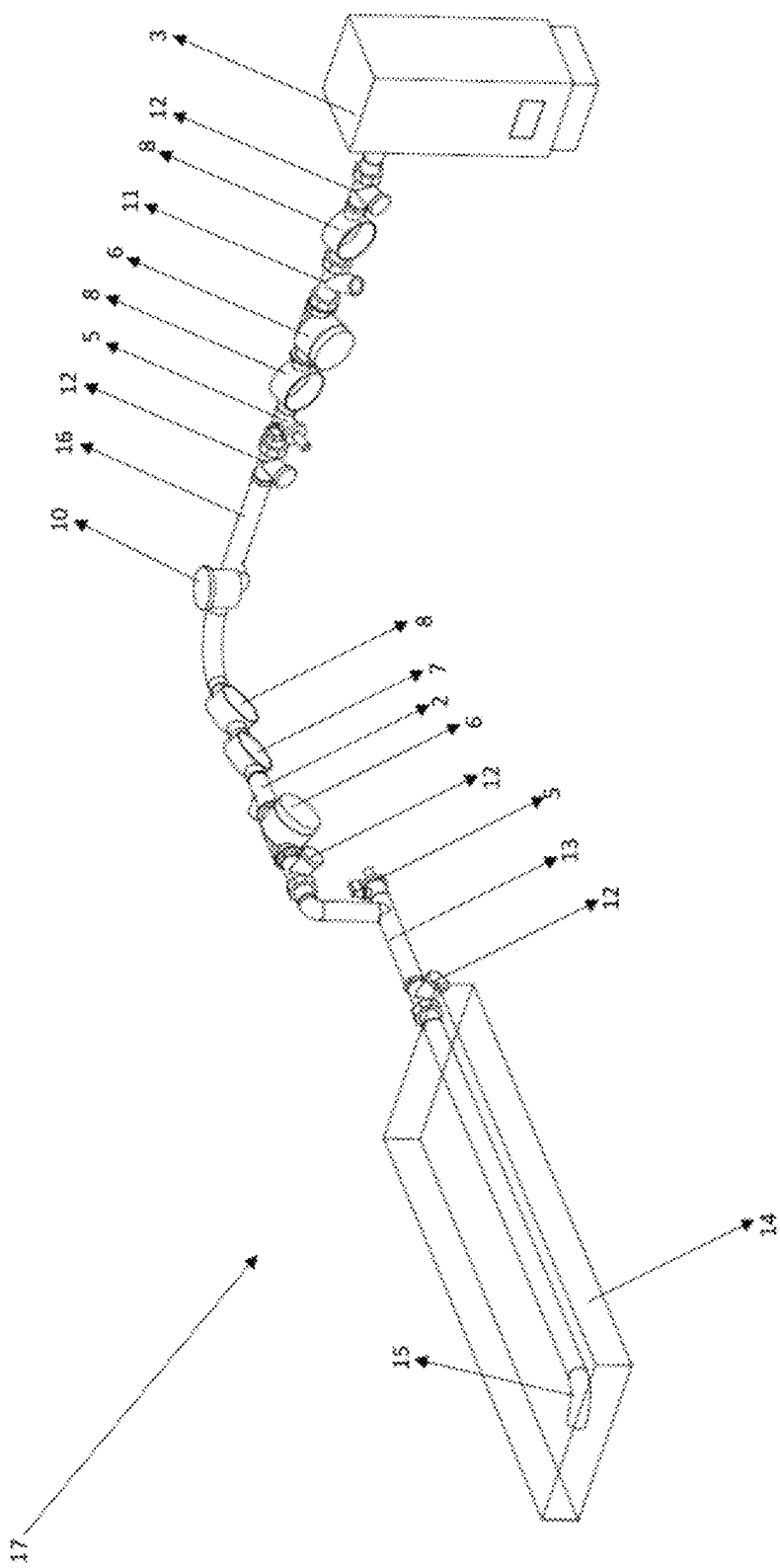
FIG. 2. shows a part of an underfloor heating and/or cooling system supplying a heated medium when it is used to heat the feed; and supplying a cooled medium when it is used to cool the feed.
Figure 3:
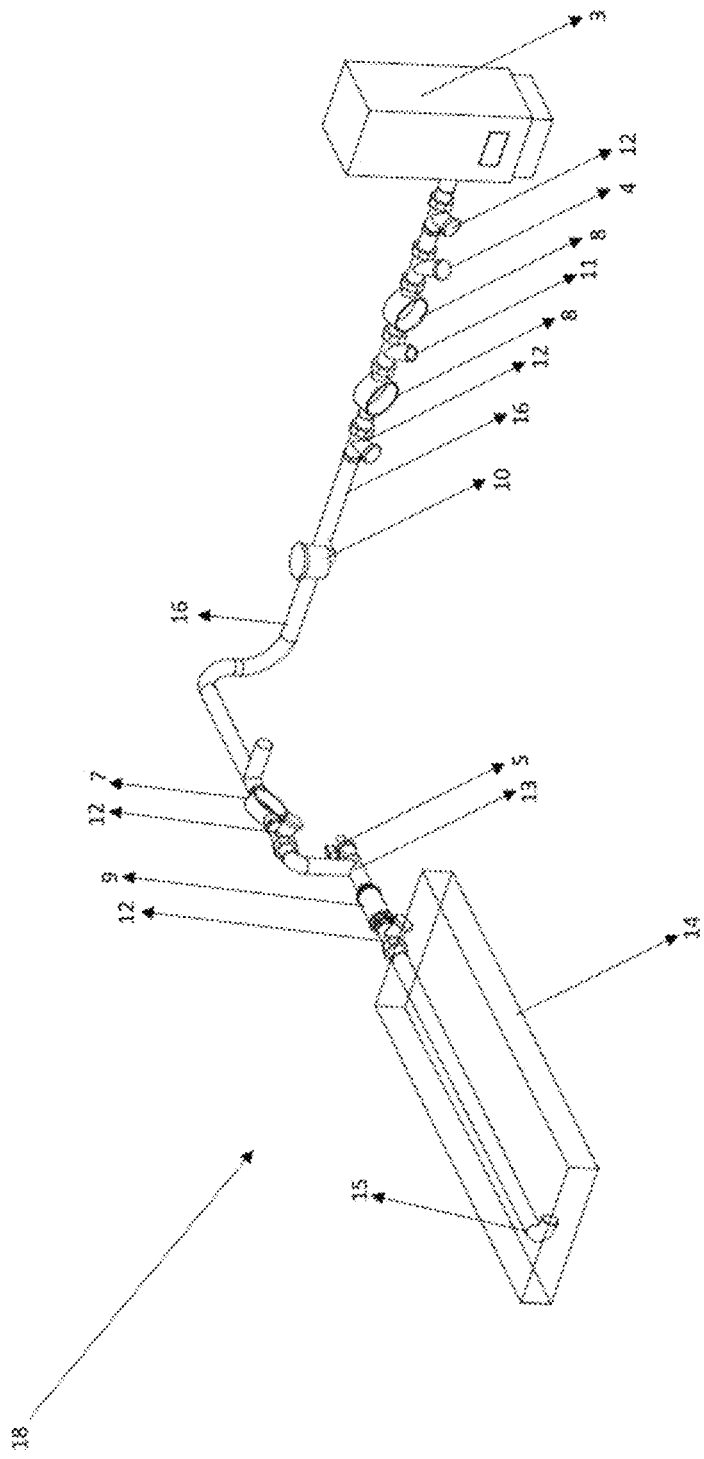
FIG. 3. shows a part of an underfloor heating and/or cooling system supplying a cooled medium when it is used to heat the feed, and supplying a heated medium when it is used to cool the feed.

Example 1: Construction of an Underfloor Heating and/or Cooling System for a Breeding Line for Breeding and Rearing Insects The underfloor feed heating and/or cooling system 1 for heating/cooling the feed in insect breeding (FIG. 1) consists of two parts of a closed heating-cooling medium circulation system. The first part of the system (FIG. 2) is connected at the outlet via the shut-off valve 12 to the heat exchanger 3 and constitutes the circuit supplying 17 the system with the heated/cooled heating-cooling medium. The second part of the system (FIG. 3) return circuit 18 serves to receive the cooled/heated heating-cooling medium and transfer it to the heat exchanger 3, where it is again heated/cooled. The circuits 17 and 18 are connected via heating-cooling pipes 15, which are embedded or otherwise permanently placed in the floor constituting the breeding surface 14. The method of permanently placing (integrating the pipes 15 into the heating/cooling surface/breeding surface 14) in the breeding surface 14 (floor) of the heating-cooling pipes is known in the field of construction. It should be made clear, for the sake of clarity, that by breeding surface 14 is meant a fragment of the floor or substrate on which the breeding is carried out. By permanently integrating the heating-cooling pipes 15 into the breeding surface 14, it should be understood that the heating-cooling pipes 15 are placed in a given fragment of the breeding surface on which insects are to be bred and, e.g., that the pipes are embedded in the given fragment of the breeding surface by filling it with a mass, so that the pipes 15 and the breeding surface 14 form a whole. The filling mass may be any building mass or any polymeric mass, a mixture thereof or any other mass known in the field of construction. The construction of the surface, in terms of construction, is of any design, but with the condition that the breeding surface 14 conducts heat well. Hence, the material required for its construction should provide good thermally conductive properties. The breeding surface 14 may comprise, at the point of direct contact with the breeding mass which is to be heated by the system 1, any thermally conductive material. The breeding surface may also be entirely made of such material. It is preferable if it is made of metal, e.g. copper, steel or aluminum, synthetic material, ceramic or concrete, or if the breeding surface is provided with a conveyor belt. However, stainless steel seems to be the best solution due to its ease of cleaning, approval for contact with food and feed materials and relatively low operating costs.

Each part of the system consists of the following constructional elements:
- a system of heating-cooling pipes 15 of oxygen-crosslinked polyethylene (PEX) discharging heat from the medium to the feed or transferring cold from the medium to the feed on breeding surfaces 14 with a system of shut-off valves 12;
- a system of filters 11, shut-off valves 12, vents 10;
- set of temperature sensors 7 and pressure sensors 8 for heating-cooling medium;
- heat exchanger 3, as a heat source in the form of a gas furnace or in the form of a heat pump as a source of both heat and cooling;
- a system of pipes 16 of carbon steel supplying the heating-cooling medium from the heat exchanger 3 to the distributor 13 supplying the PEX heating/cooling pipe system 15 with the heating-cooling medium;
- drain valves 5 for heating-cooling medium.

The part supplying the system with heated/cooled medium additionally comprises a drain valve 5, which enables draining the medium e.g. when servicing the line or needing to replace the medium, placed downstream of the first circulation pump 6 and a three-way valve 2 directly connected to upstream of the second circulation pump 6, it enables mixing the medium from both parts of the system in order, e.g. to regulate the pressure or temperature. Whereas the part of the system receiving the cooled/heated heating-cooling medium comprises a pressure equalization valve 4, placed upstream of the shut-off valve 12 connecting at the outlet of the second part of the system with the heat exchanger 3.

The heating-cooling medium in the underfloor system for heating the feed in insect breeding was water, heated by a gas furnace or heat pump as heat exchanger 3. The temperature of water leaving the furnace was 39° C. The heated water was discharged from the furnace or heat pump through a steel pipe 16 placed in an insulating bundle to minimize heat loss. The intensity of the water flow was 0.16 m$^3$/h. The water, after passing through a solid particle filter 11 (mesh filter), was pumped by a circulation pump 6 to the distributor 13 of the heating-cooling installation placed on the production surface of the breeding surface 14 for insect breeding and rearing.

In order to discharge the heat to the feed, heated water is fed from the distributor 13 into a heating-cooling installation consisting of heating-cooling pipes 15, made of PEX, which are embedded in two rows 20 cm apart from each other along the breeding surface 14 intended for rearing insects. The heating-cooling pipes 15 are embedded directly in the breeding surfaces 14, onto which the feed for the bred insects is then laid. The laid feed has a temperature lower than the heating-cooling medium and of about 20° C., as a result of which it begins to receive its heat, until it reaches a thermal equilibrium at the level of 39° C. The water, cooled to a temperature of about 38° C., returns through the pipe system 15 to the heating device (heat exchanger 3) maintaining a constant temperature of the medium in the heating system.

Temperature sensors 7 as well as pressure sensors 8 of the heating-cooling medium are placed at specific points in the heating-cooling system, providing information about its physical parameters. A rotameter 9 is also installed at the entry to the breeding surfaces 14 in order to measure the flow rate of the medium. The gas boiler or heat pump is provided with an automatic temperature regulation allowing for any temperature setting in the range from 7 to 50° C.

Figure 4:
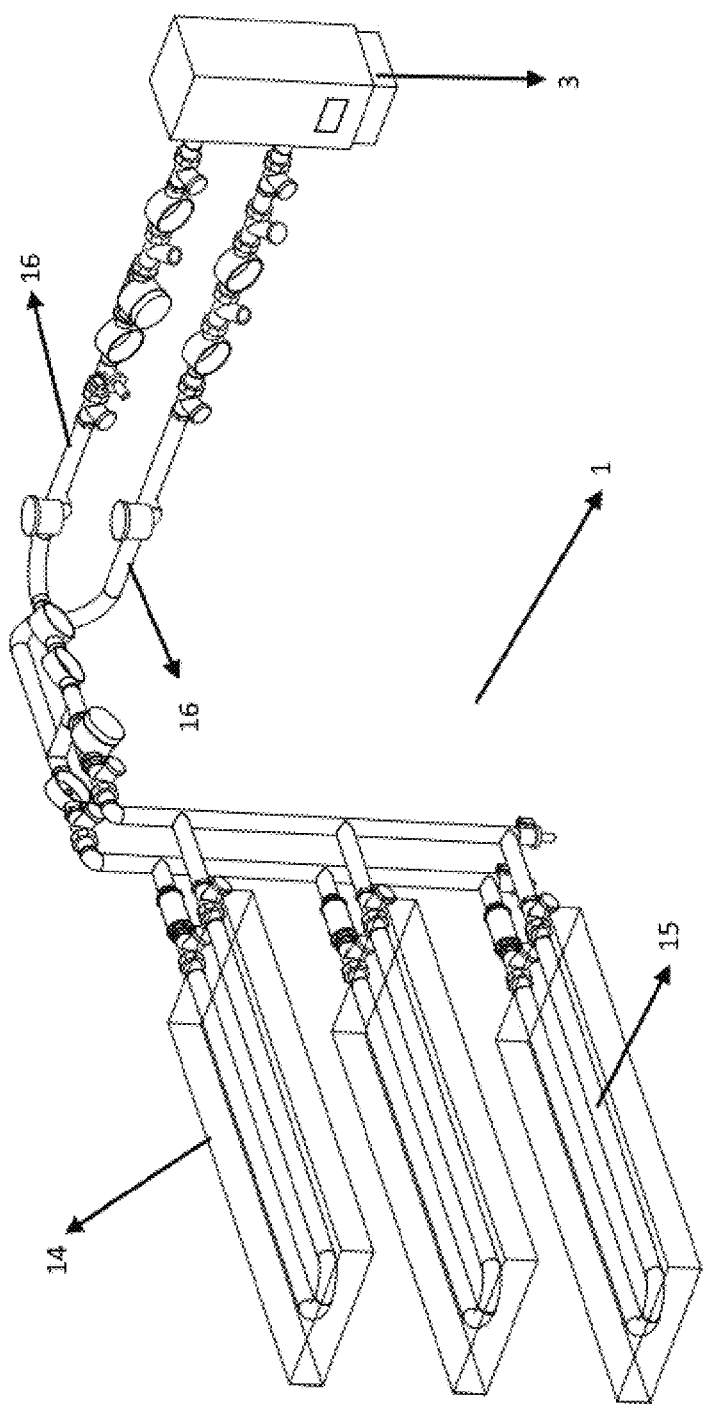
FIG. 4 shows a diagram of an underfloor heating/cooling system of a breeding surface for breeding invertebrates with multiple layouts of breeding surface.

The underfloor heating system 1 may also comprise a multiple layout of heating-cooling pipes 15, i.e. the heating-cooling medium supply circuit 17 and the return circuit 18 for the cooled medium may comprise a heating-cooling pipe layout led out to more than one breeding surface 14. FIG. 4 illustrates such a variant of embodiment of the invention. This is only an example showing that the breeding surfaces 14 may be more than one, and their number depends only on the adjustment of the flow in the remaining part of the system 1 and on the capacity of the heat exchanger 3.

Example 2: Use of an Underfloor Heating/Cooling System for Heating the Feed

Tests carried out during the testing of the system have shown that the feed in the described system heats up three times faster than in the open air, which translates into effectiveness and speed of use of this system in providing appropriate thermal conditions for insects.

TABLE 1

Figure 5:
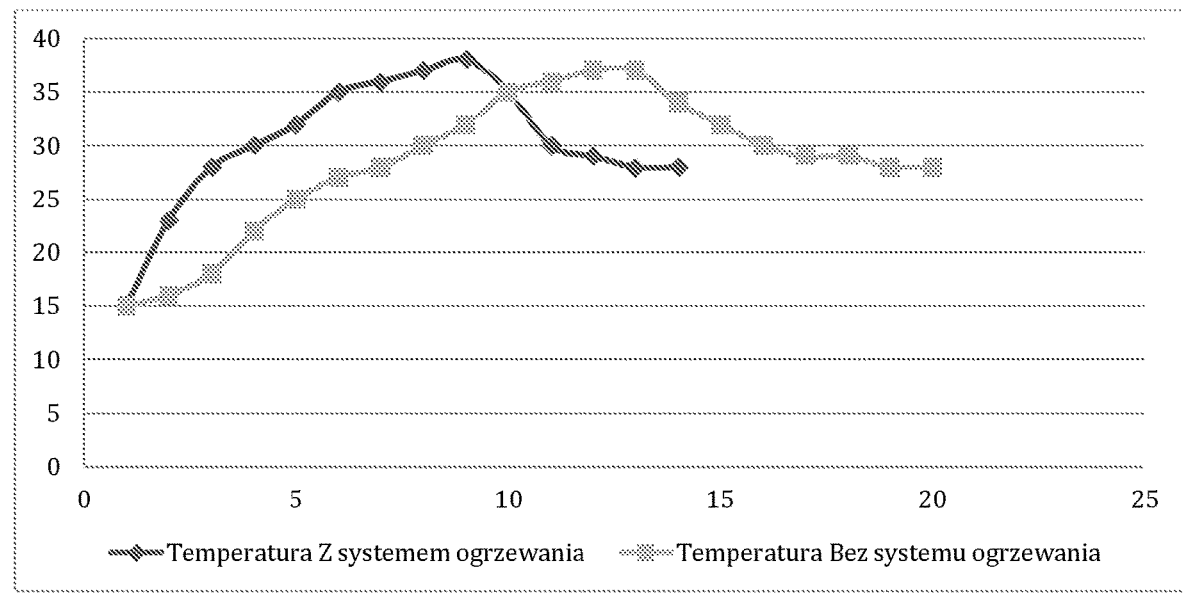
FIG. 5. shows a temperature dependence on feed heating time (A), shows a cross-section of a breeding surface (one storey of a breeding line) with a conveyor belt with lateral sidewalls with bending, here preferred embodiment with double bending (B).
Figure 5:
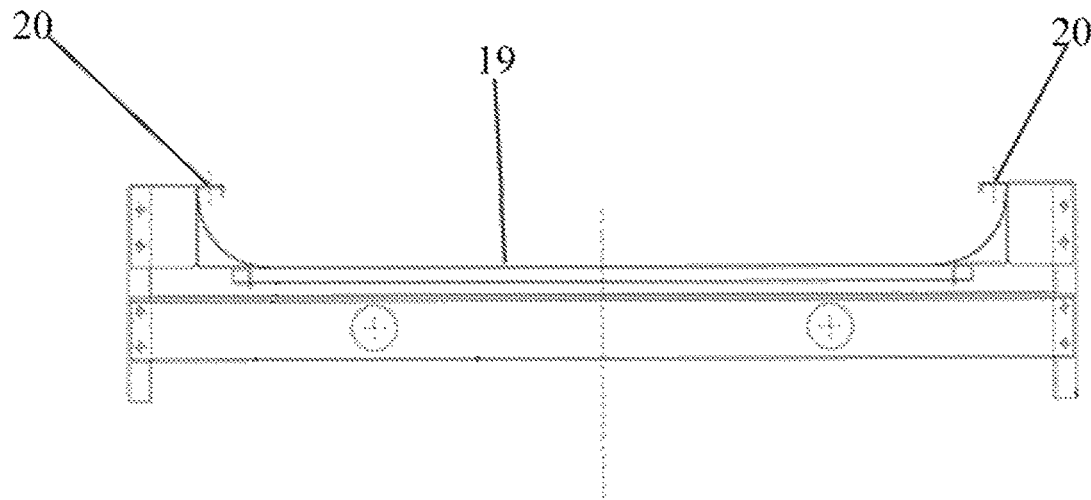
Figure 6:
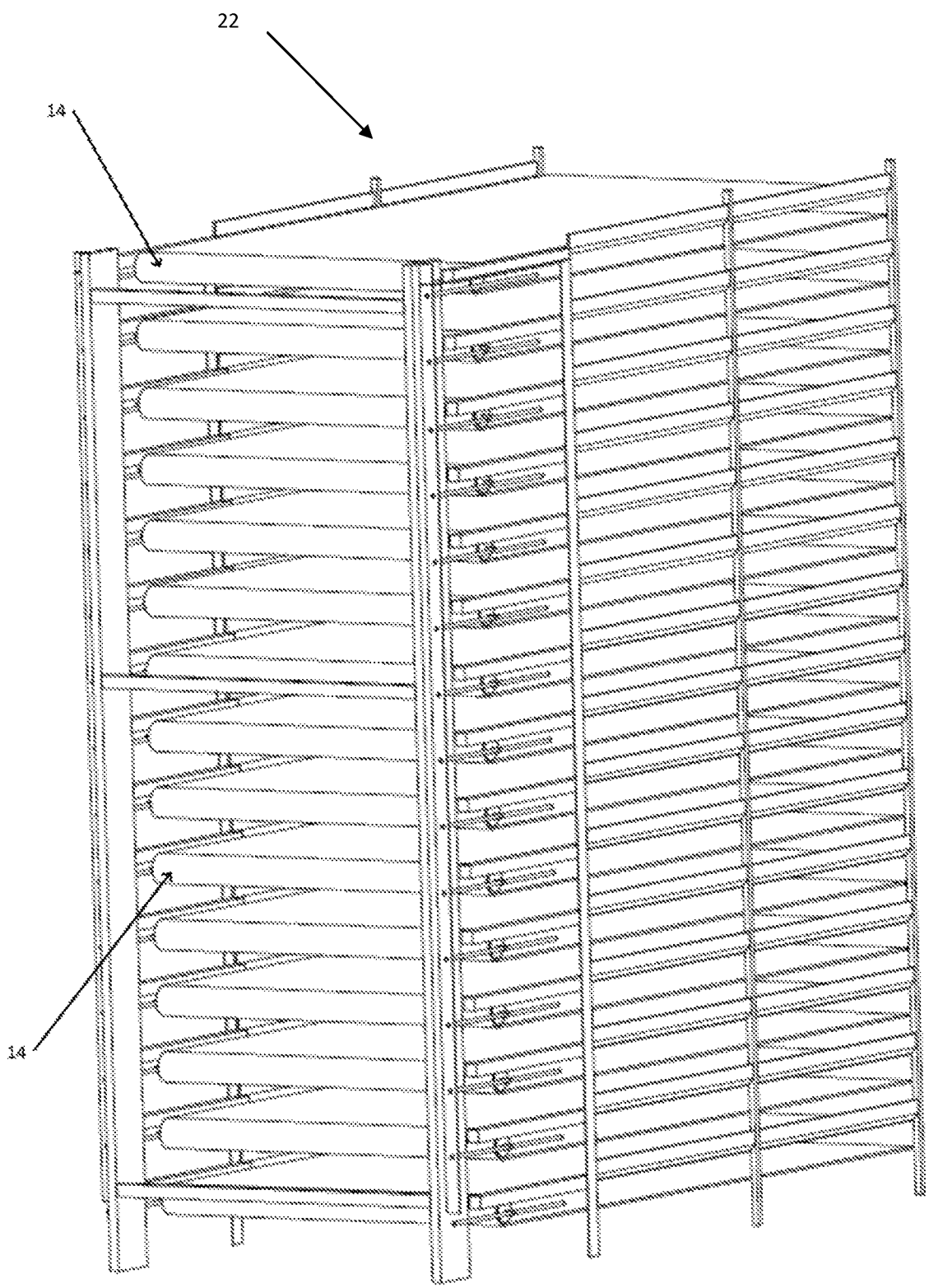
FIG. 6. shows a diagram of a fragment of a production line with a storey layout of breeding surfaces, for clarity an underfloor feed heating and/or cooling system has been omitted from the figure.

Heating the feed with and without installed heating/cooling system (FIG. 5 A)

| | | Temperature ° C. | |
|---|---|---|---|
| Days | Hour | With the heating system | Without the heating system |
| 0 | 06:00 | 15 | 15 |
|   | 18:00 | 24 | 16 |
| 1 | 06:00 | 28 | 18 |
|   | 18:00 | 31 | 22 |

TABLE 1-continued

Heating the feed with and without installed heating/cooling system (FIG. 5 A)

| | | Temperature ° C. | |
|---|---|---|---|
| Days | Hour | With the heating system | Without the heating system |
| 2 | 06:00 | 34 | 25 |
| | 18:00 | 36 | 27 |
| 3 | 06:00 | 37 | 28 |
| | 18:00 | 37 | 30 |
| 4 | 06:00 | 38 | 32 |
| | 18:00 | 37 | 35 |
| 5 | 06:00 | 35 | 36 |
| | 18:00 | 33 | 37 |
| 6 | 06:00 | 33 | 37 |
| | 18:00 | 33 | 34 |
| 7 | 06:00 | | 32 |
| | 18:00 | | 30 |
| 8 | 06:00 | | 29 |
| | 18:00 | | 29 |
| 9 | 06:00 | | 28 |
| | 18:00 | | 28 |

TABLE 2

Summary of results for heating the feed

| | Feed heating | No feed heating |
|---|---|---|
| Type of feed | Fruit and vegetable mix | Fruit and vegetable mix |
| Layer thickness | 5-7 cm | 5-7 cm |
| Heating duration | 6 days | 9 days |

Example 3: Comparative Measurement of Body Weight of Bred Insects and Feed Conversion Ratio Comparative measurements were carried out using the breeding method according to the invention and known breeding methods without heating/cooling the feed.

Insects bred using the described breeding method according to the invention are characterized by a 25% faster fattening, achieving a 7.5% higher body weight at the end of the fattening, as well as a reduction of up to 12% in the feed conversion ratio (FCR).

TABLE 3

Results of an insect rearing experiment on surfaces with and without heating the feed.

| | Feed heating | No feed heating |
|---|---|---|
| Type of feed | Fruit and vegetable mix | mix. Fruit and vegetable mix |
| Insect species | H. illucens | H. illucens |
| BWG kg/m$^2$ | 6.51 | 5.93 |
| FCR | 6.81 | 7.5 |
| Survival | 92% | 51% |
| Rearing time | 6 | 8 |

Example 4: Measurement of Insect Survival

Insects bred using the method according to the invention were characterized by reduced stress related to feeding the larvae, which increased their survival, which was observed to be up to 41% higher when using an underfloor feed heating and/or cooling system 1 or a heated production surface, as compared to the standard rearing method where entire holding rooms are heated (Tab. 3).

Example 5: Use of an Underfloor Heating/Cooling System for Cooling the Feed

Tests carried out during the testing of the system have shown that the feed cools down quicker with an underfloor heating/cooling system for cooling the feed in the case of too high temperatures than in the open air, which translates into the effectiveness and speed of the use of this system in providing appropriate and stabilised close to optimal thermal conditions for the insects, as well as cooling them down and avoiding overheating or even killing them due to too high temperatures.

TABLE 4

Cooling the feed with and without installed underfloor heating/cooling system.

| | | Temperature | |
|---|---|---|---|
| Days | Hour | With cooling system | Without cooling system |
| 1 | 06:00 | 38 | 38 |
| | 18:00 | 35 | 38 |
| 2 | 06:00 | 30 | 37 |
| | 18:00 | 29 | 37 |
| 3 | 06:00 | 28 | 36 |
| | 18:00 | 28 | 34 |
| 4 | 06:00 | 28 | 32 |
| | 18:00 | 28 | 31 |
| 5 | 06:00 | | 30 |
| | 18:00 | | 30 |
| 6 | 06:00 | | 29 |
| | 18:00 | | 28 |
| 7 | 06:00 | | 28 |
| | 18:00 | | 28 |

TABLE 5

Summary of results for cooling the feed

| | With feed cooling | No feed cooling |
|---|---|---|
| Type of feed | Fruit and vegetable mix | Fruit and vegetable mix |
| Layer thickness | 5-7 cm | 5-7 cm |
| Cooling duration | 3 days | 6 days |

Example 6: Drying of Fertiliser

In this example of embodiment (Tab. 6 and Tab. 7), the use of an underfloor feed heating and/or cooling system and a heated production surface according to the invention for the drying of secondary metabolites by heating the breeding surface 14 after the production of insects including faeces, being a component of the fertilizer, is shown.

TABLE 6

Figure 7:
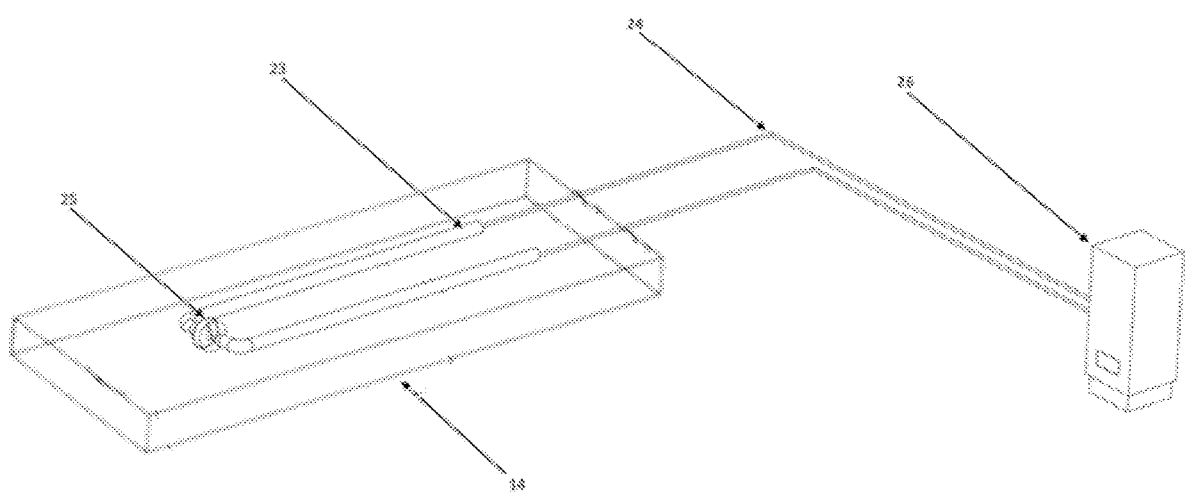
FIG. 7 shows a breeding surface with an underfloor feed heating system which is an electrical underfloor heating system permanently placed in the breeding surface.

Results of experiment showing drying of faeces/fertiliser (FIG. 7)

| | Feed moisture | |
|---|---|---|
| Rearing days | Heating system % dry mass | No heating % dry mass |
| 1 | 25 | 25 |
| 2 | 30 | 27 |
| 3 | 40 | 30 |
| 4 | 60 | 35 |
| 5 | 70 | 40 |
| 6 | 80 | 50 |
| 7 | | 60 |

TABLE 6-continued

Results of experiment showing drying of faeces/fertiliser (FIG. 7)

| | Feed moisture | |
|---|---|---|
| Rearing days | Heating system % dry mass | No heating % dry mass |
| 8 | | 70 |
| 9 | | 80 |
| 10 | | |

TABLE 7

Summary of results for drying of fertilizer

| | Feed heating | No feed heating |
|---|---|---|
| Start moisture | 25% dry mass | 25% dry mass |
| Final moisture | 80% dry mass | 80% dry mass |
| Type of feed | Fruit and vegetable mix | Fruit and vegetable mix |
| Layer thickness | 5-7 cm | 5-7 cm |
| Heating duration | 6 days | 9 days |

Example 7: Construction of an Electrical Underfloor Heating System for Insect Breeding and Rearing A heated production surface for rearing and/or breeding insects and/or larval forms of insects with an electrical underfloor heating system for heating the feed in insect breeding is shown in FIG. 7 and includes an electrical underfloor heating system 21 comprising a heating cable 23 embedded or otherwise permanently placed in the floor constituting the breeding surface 14. The method of permanently placing (integrating the heating cable 23 into the heating surface in the breeding surface 14 (floor) is known in the field of construction. It should be made clear, for the sake of clarity, that the breeding surface 14 should be understood as a fragment of the floor or substrate on which the breeding is carried out. By permanently integrating the electrical heating cables 23 into the breeding surface 14, it should be understood as placing the cables in a given fragment of the breeding surface 14, on which insect breeding is carried out, and, e.g., embedding these cables in the given fragment of the breeding surface 14 by filling it with a mass, in such a way that the heating cables 23 and the breeding surface form a whole. The filling mass may be any building mass or any polymeric mass, a mixture thereof or any other mass known in the construction field. The construction of the surface, in terms of construction, is of any design, but with the condition that the breeding surface 14 conducts heat well. Hence, the material required for its construction should provide good thermally conductive properties. The breeding surface 14 may comprise, in direct contact with the breeding mass (feed and insects) which is to be heated by the system, any thermally conductive material. The breeding surface may also be entirely made of such a material.

It is preferred for it to be of metal, e.g. copper, steel or aluminum, plastic, ceramic or concrete. However, stainless steel seems to be the best solution due to its ease of cleaning, approval for contact with food and feed materials and relatively low operating costs, or a breeding surface provided with a conveyor belt.

An electrical underfloor feed heating system for insect breeding and rearing includes the following constructional elements:

heating cable 23 placed in the breeding surface 14;
connection wires 24;
feed temperature sensor 25 on the breeding surface;
control-power unit 26, which powers the heating cable and controls the operation of the heating cable.

In order to transfer the heat to the feed, the heating cable 23 is powered by a current with predetermined parameters (voltage, frequency, amperage) controlled by the control-power unit 26 on the basis of data received from the feed temperature sensor 25. The control-power unit 26 is powered by an external power source coming from the mains or from a battery or a power generator. The control-power unit 26 is connected to the heating cable 23 via connection wires 24. The control-power unit allows to automatically change the parameters of the outgoing current in order to maintain the temperature of the heating cable within a predetermined temperature range from 7 to 50° C., preferably 20° C.–48° C., more preferably to 25-35° C., more preferably to 28-32° C. or other or zonally different.

An electrical underfloor heating system constituting a feed heating part in a heated production surface for rearing and/or breeding of insects and/or larval forms of insects may also comprise multiple layout of heating cables and the cables may be routed to more than one breeding surface.

When using an electrical underfloor feed heating system, the same results were obtained as in the case of an underfloor heating and/or cooling system with a closed flow of the heating-cooling medium, included in Tab. 3, 6, 7. The use of an electrical underfloor feed heating system allows to heat the feed to the desired temperature and stabilize it within the selected temperature range so as to ensure optimum breeding conditions for a given insect species (temperature optimum).

LIST OF REFERENCE SIGNS

1—underfloor feed heating and/or cooling system
2—three-way valve
3—heat exchanger
4—balancing valve
5—drain valve
6—circulation pump
7—temperature sensor
8—pressure sensor
9—rotameter
10—vent
11—solid particle filter
12—shut-off valves
13—distributor
14—breeding floor/surface
15—heating-cooling pipes (e.g. of PEX plastic)
16—pipes e.g. steel pipes
17—supply circuit
18—return circuit
19—conveyor belt
20—lateral sidewalls
21—electrical underfloor heating system
22—fragment/segment of a multi-storey production surface
23—heating cable
24—connection wires
25—feed temperature sensor
26—control-power unit

The invention claimed is:
1. A production surface for rearing and/or breeding of insects and/or larval forms of insects, comprising:

a) at least one breeding surface for breeding insects for laying feed thereon,
b) an underfloor feed heating and/or cooling system with a closed flow of a heating-cooling medium for heating and/or cooling the feed on the at least one breeding surface,
wherein the underfloor feed heating and/or cooling system comprises at least one heating-cooling medium supply circuit and at least one heating-cooling medium return circuit connected to each other, and the heating-cooling medium supply circuit and the heating-cooling medium return circuit are fluidly connected to a heat exchanger for heating/cooling the heating-cooling medium, and the heating-cooling medium supply circuit and the heating-cooling medium return circuit comprise distributors for the heating-cooling medium, and heating-cooling pipes of thermally conductive material are connected to the heating-cooling medium distributors via a shut-off valve for distribution of heat and/or cold on the at least one breeding surface,
wherein the heating-cooling pipes of thermally conductive material of the underfloor system for heating/cooling the feed on the at least one breeding surface are permanently integrated directly into said at least one breeding surface for laying the feed thereon,
wherein the heating-cooling pipes of thermally conductive material are placed under the at least one breeding surface in at least two rows parallel to each other,
wherein the heating-cooling medium supply circuit and the heating-cooling medium return circuit are connected via a three-way valve,
wherein the rearing and/or breeding of insects and/or larval forms of insects concern insects of the orders Coleoptera and/or Diptera.

2. The production surface according to claim 1, wherein the heating medium is water or glycol.

3. The production surface according to claim 1, wherein the heat exchanger provides heating/cooling of the heating-cooling medium to a temperature in a range of 15-50° C.

4. The production surface according to claim 1, wherein the at least one breeding surface is made of a material with thermally conductive properties selected from the group consisting of: copper, aluminum, plastic, ceramic, concrete, and steel, including but not limited to, stainless steel.

5. The production surface according to claim 1, wherein the heating-cooling pipes are made of a material with thermally conductive properties selected from the group consisting of: copper, steel, aluminum, and synthetic material.

6. The production surface according to claim 1, wherein the heat exchanger is based on a source of electrical energy, gas, or use of heat/cooling pumps or recuperation.

7. The production surface according to claim 1, wherein the heating-cooling pipes arranged in the at least one breeding surface form at least two rows of heating-cooling pipes spaced from each other from 1 to 30 cm.

8. The production surface according to claim 1, wherein the heating-cooling medium supply circuit and the heating-cooling medium return circuit comprise a system of shut-off valves, drain valves, vents, at least one temperature sensor and at least one pressure sensor, which are fluidly connected to each other.

9. The production surface according to claim 1, wherein the heating-cooling medium return circuit comprises a rotameter or the heating-cooling medium supply circuit comprises a solid particle filter.

10. A method for breeding insects using the production surface of claim 1, comprising a step of rearing and/or breeding insects and/or larval forms of insects,
wherein in said step the feed is heated and/or cooled by means of the underfloor feed heating and/or cooling system with the closed flow of the heating-cooling medium for heating/cooling the feed on the at least one breeding surface, and
wherein the step of rearing and/or breeding insects and/or larval forms of insects is carried out on the production surface of claim 1.

11. The production surface according to claim 1, wherein the at least one breeding surface comprises at least one storey, provided with an autonomous conveyor belt.

12. The production surface according to claim 11, wherein a plurality of profiled lateral sidewalls are arranged bilaterally along a direction of movement of the autonomous conveyor belt and edges of the plurality of profiled lateral sidewalls are bent inwards.

13. A method for breeding insects comprising:
a) feed at a storage temperature is laid on a breeding surface adapted for laying feed for breeding insects,
b) insect feed is laid on the breeding surface, wherein the breeding surface is heated and/or cooled by means of an underfloor feed heating and/or cooling system in a closed system, wherein the underfloor feed heating and/or cooling system includes:
c) at least one heating-cooling medium supply circuit and at least one heating-cooling medium return circuit connected to each other, and the heating-cooling medium supply circuit and the heating-cooling medium return circuit are fluidly connected to a heat exchanger for heating/cooling a heating-cooling medium, and the heating-cooling medium supply circuit and the heating-cooling medium return circuit comprise heating-cooling medium distributors, and heating-cooling pipes made of thermally conductive material are connected to the heating-cooling medium distributors via a shut-off valve providing heat/cooling distribution on the breeding surface, wherein the pipes made of thermally conductive material of the system for heating/cooling the feed on the breeding surface are permanently integrated into the breeding surface, wherein the heating-cooling pipes of thermally conductive material are arranged in at least two rows parallel to each other, wherein the heating-cooling medium supply circuit and the heating-cooling medium return circuit are connected via a three-way valve, wherein rearing and/or breeding of insects and/or larval forms of insects concern insects of the orders Coleoptera and/or Diptera.

14. The method for breeding insects according to claim 13, wherein the feed is heated/cooled to a temperature in a range of 7° C. to 50° C. or wherein the heat exchanger provides heating/cooling of the heating-cooling medium to a temperature in a range of 7° C. to 50° C.

15. The method for breeding insects according to claim 13, wherein the bred insects are placed in drawer, box, or self-supporting systems.

16. The method for breeding insects according to claim 13,
wherein the heating medium is water or glycol.

17. The method for breeding insects according to claim 13, wherein the heating-cooling pipes are made of a material with thermally conductive properties selected from a group consisting of: copper, steel, aluminum, and synthetic material.

18. The method for breeding insects according to claim 13, wherein the heat exchanger is based on an electrical or gas energy source, or use of heat pumps or heat/cold recuperation.

19. The method for breeding insects according to claim 13, wherein the heating-cooling pipes arranged in the breeding surface form at least two rows of heating-cooling pipes spaced from each other by from 1 to 30 cm.

20. The method for breeding insects according to claim 13, wherein the heating-cooling medium supply circuit and the heating-cooling medium return circuit include a system of shut-off valves, drain valves, vents, at least one temperature sensor and at least one pressure sensor, and are fluidly connected to each other.

21. The method for breeding insects according to claim 13, wherein the heating-cooling medium return circuit includes a rotameter or the heating-cooling medium supply circuit comprises a solid particle filter.

22. The method for breeding insects according to claim 13, wherein the at least one breeding surface comprises at least one storey, provided with an autonomous conveyor belt.

23. The method for breeding insects according to claim 22, wherein a plurality of profiled lateral sidewalls are arranged bilaterally along a direction of movement of the autonomous conveyor belt and edges of the plurality of profiled lateral sidewalls are bent inwards.

24. Use of an underfloor feed heating and/or cooling system with a closed flow, wherein the system is used to heat and/or cool feed on a breeding surface for breeding insects,
wherein said underfloor feed heating and/or cooling system includes at least one heating-cooling medium supply circuit and at least one heating-cooling medium return circuit connected to each other, and the heating-cooling medium supply circuit and the heating-cooling medium return circuit are fluidly connected with a heat exchanger for heating/cooling a heating-cooling medium, and the heating-cooling medium supply circuit and the heating-cooling medium return circuit comprise heating-cooling medium distributors, and heating-cooling pipes of thermally conductive material for distribution of heat/cooling on the breeding surface are connected to the heating-cooling medium distributor via a shut-off valve,
wherein the heating-cooling pipes of thermally conductive material of the system for heating/cooling the feed on the breeding surface are permanently integrated into the breeding surface for laying the feed for breeding insects thereon,
wherein the heating-cooling pipes of thermally conductive material are arranged in at least two rows parallel to each other,
wherein the heating-cooling medium supply circuit and the heating-cooling medium return circuit are connected via a three-way valve,
wherein the rearing and/or breeding of insects and/or larval forms of insects concern insects of the orders Coleoptera and/or Diptera,
wherein the breeding surface comprises at least one story, provided with an autonomous conveyor belt with profiled lateral sidewalls arranged bilaterally along a direction of movement of the conveyor belt, and the edges of the lateral sidewalls are bent inwards.

25. The use of the system according to claim 24, wherein the heating-cooling medium is water or glycol.

26. The use of the system according to claim 24, wherein the heat exchanger provides heating/cooling of the heating-cooling medium to a temperature in a range of 15-50° C.

27. The use of the system according to claim 24, wherein the heating-cooling pipes are made of a material with thermally conductive properties selected from a group consisting of: copper, steel, aluminum, and plastic.

28. The use of the system according to claim 24, wherein the heat exchanger is based on an electrical or gas energy source or use of heat pumps or heat/cold recuperation.

29. The use of the system according to claim 24, wherein the heating-cooling pipes arranged in the breeding surface form at least two rows of heating-cooling pipes spaced from each other by from 1 to 20 cm.

30. The use of the system according to claim 24, wherein the heating-cooling medium supply circuit and the heating-cooling medium return circuit include a system of shut-off valves, drain valves, vents, at least one temperature sensor and at least one pressure sensor, and are fluidly connected to each other.

31. The use of the system according to claim 24, wherein the heating-cooling medium return circuit includes a rotameter or the heating-cooling medium supply circuit includes a solid particle filter.

32. The use of the system according to claim 24, wherein the breeding surface is made of a material with thermally conductive properties selected from a group consisting of: copper, steel, aluminum, plastic, ceramic, and concrete.

33. A heated production surface for rearing and/or breeding of insects and/or larval forms of insects, comprising:
a) at least one breeding surface for breeding insects for laying feed thereon,
b) an underfloor feed heating system comprising an electrical underfloor heating system permanently placed in the at least one breeding surface,
wherein the electrical underfloor feed heating system is selected from a heating mat or a heating cable.

34. The heated production surface for rearing and/or breeding of insects and/or larval forms of insects according to claim 33, wherein the electrical underfloor heating system comprises a heating cable placed in the at least one breeding surface connected via connection wires to a control-power unit controlling the operation of the heating cable, said control-power unit being connected to an energy source.

35. A method for breeding insects comprising a step of rearing and/or breeding insects and/or larval forms of insects in which the feed is heated using a heated production surface for rearing and/or breeding insects and/or larval forms of insects, which comprises:
a) at least one breeding surface for breeding insects for laying feed thereon,
b) an underfloor feed heating system comprising an electrical underfloor heating system permanently placed in the at least one breeding surface,
wherein the electrical underfloor feed heating system is selected from a heating mat or a heating cable.

36. The method for breeding insects according to claim 35, wherein the electrical underfloor heating system comprises a heating cable placed in the at least one breeding surface connected via connection wires to a control-power unit controlling the operation of the heating cable, said control-power unit being connected to an energy source.

* * * * *